(12) United States Patent
Wei et al.

(10) Patent No.: US 7,711,425 B2
(45) Date of Patent: May 4, 2010

(54) DEFIBRILLATION THRESHOLD PREDICTION METHODS AND SYSTEMS

(75) Inventors: Xuan Wei, Roseville, MN (US); Robert J. Sweeney, Woodbury, MN (US); Joseph M. Bocek, Seattle, WA (US); Scott A. Meyer, Rochester, MN (US); Jeffrey E. Stahmann, Ramsey, MN (US); Yi Zhang, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 930 days.

(21) Appl. No.: 11/208,923

(22) Filed: Aug. 22, 2005

(65) Prior Publication Data

US 2007/0043395 A1    Feb. 22, 2007

(51) Int. Cl.
*A61N 1/08* (2006.01)
*A61N 1/39* (2006.01)

(52) U.S. Cl. ............... 607/28; 607/5; 607/7; 607/8
(58) Field of Classification Search .............. 607/5, 607/7, 8, 28
See application file for complete search history.

(56) References Cited

U.S. PATENT DOCUMENTS

| | | | |
|---|---|---|---|
| 5,318,597 A | 6/1994 | Hauck et al. | |
| 5,346,506 A | 9/1994 | Mower et al. | |
| 5,397,336 A | 3/1995 | Hirschberg et al. | |
| 5,531,770 A | 7/1996 | Kroll et al. | |
| 5,540,724 A | 7/1996 | Cox | |
| 5,662,687 A | 9/1997 | Hedberg et al. | |
| 5,683,431 A | 11/1997 | Wang | |
| 5,925,067 A | 7/1999 | Lu | |
| 5,978,705 A | 11/1999 | KenKnight et al. | |
| 5,999,852 A | 12/1999 | Elabbady et al. | |
| 6,076,015 A | 6/2000 | Hartley et al. | |
| 6,169,923 B1 | 1/2001 | Kroll | |
| 6,353,761 B1 | 3/2002 | Conley et al. | |

(Continued)

FOREIGN PATENT DOCUMENTS

WO    WO-2007024471 A1    3/2007

(Continued)

OTHER PUBLICATIONS

"International Search Report and Written Opinion for Application No. PCT/US2006/030829, Date Mailed Dec. 13, 2006", 13 Pages.

(Continued)

*Primary Examiner*—Carl H Layno
*Assistant Examiner*—Natasha N Patel
(74) *Attorney, Agent, or Firm*—Schwegman, Lundberg & Woessner, P.A.

(57) ABSTRACT

A nondefibrillating and nonfibrillation-inducing energy is delivered at a first internal thoracic location. A first resulting electrical signal is detected at a second internal thoracic location in or near a target region of a heart. A first defibrillation threshold is estimated using the nondefibrillating and non-fibrillation-inducing energy, the first resulting electrical signal, and a target electric field strength. The defibrillation threshold represents an energy that when delivered at the first internal thoracic location creates an electric field strength in the target region of the heart that meets or exceeds the target electric field strength.

40 Claims, 7 Drawing Sheets

U.S. PATENT DOCUMENTS

| | | | |
|---|---|---|---|
| 6,363,281 | B1 | 3/2002 | Zhu et al. |
| 6,675,042 | B2 | 1/2004 | Swerdlow et al. |
| 6,751,502 | B2 | 6/2004 | Daum et al. |
| 6,859,664 | B2 | 2/2005 | Daum et al. |
| 6,904,314 | B1 * | 6/2005 | Brewer et al. ............. 607/7 |
| 6,978,178 | B2 | 12/2005 | Sommer et al. |
| 7,643,877 | B2 | 1/2010 | Dujmovic, Jr. et al. |
| 2002/0002389 | A1 | 1/2002 | Bradley et al. |
| 2002/0133206 | A1 | 9/2002 | Daum et al. |
| 2002/0188326 | A1 | 12/2002 | Zheng et al. |
| 2003/0032989 | A1 | 2/2003 | Herleikson |
| 2003/0195569 | A1 | 10/2003 | Swerdlow et al. |
| 2004/0138714 | A1 * | 7/2004 | Daum et al. ............ 607/8 |
| 2005/0251215 | A1 | 11/2005 | Dujmovic, Jr. et al. |
| 2008/0249581 | A1 | 10/2008 | Wei |

FOREIGN PATENT DOCUMENTS

| | | |
|---|---|---|
| WO | WO-2008/123902 | 10/2008 |

OTHER PUBLICATIONS

Bessho, R., et al., "Measurement of the upper limit of vulnerability during defibrillator implantation can substitute defibrillation threshold measurement", *The International Journal of Artificial Organs*, 21 (3), (Mar. 1998), 151-160.

Birgersdotter-Green, Ulrika, et al., "Correlation of Acute and Chronic Defibrillation Threshold with Upper Limit of Vulnerability Determined in Normal Sinus Rhythm", *Journal of Interventional Cardiac Electrophysiology*, 3, (Mar. 1999), 155-161.

Church, T., et al., "A Model to Evaluate Alternative Methods of Defibrillation Threshold Determination", *PACE*, 11, (Nov. 1988), pp. 2002-2007.

Eason, J., et al., "Influence of Anisotropy on Local and Global Measures of Potential Gradient in Computer Models of Defibrillation", *Annals of Biomedical Engineering*, 26, (1998), pp. 840-849.

Ellenbogen, K. A., et al., "Immediate Reproducibility of Upper Limit of Vulnerability Measurements in Patients Undergoing Transvenous Implantable Cardioverter Defibrillator Implantation", *Journal of Cardiovascular Electrophysiology*, 9 (6), (Jun. 1998), pp. 588-595.

Ideker, R. E., "Chapter 2—Mechanisms of Defibrillation", *Defibrillation of the heart : ICDs, AEDs, and manual*, St. Louis : Mosby, (1994), 15-45.

Martin, D. J., et al., "Upper Limit of Vulnerability Predicts Chronic Defibrillation Threshold for Transvenous Implantable Defibrillators", *Journal of Cardiovascular Electrophysiology*, 8 (3), (Mar. 1997), 241-248.

Min, X., et al., "Finite element analysis of defibrillation fields in a human torso model for ventricular defibrillation", *Progress in Biophysics & Molecular Biology*, 69, (1998), pp. 353-386.

Pendekanti, R., et al., "Spatial Potential and Current Distributions Along Transvenous Defibrillation Electrodes: Variation of Electrode Characteristics", *Annals of Biomedical Engineering*, 24, (1996), pp. 156-167.

Schimpf, P. H., et al., "Effects of electrode interface impedance of finite element models of transvenous defibrillation", *Medical & Biological Engineering & Computing*, (Sep. 1995), pp. 713-719.

Sun, Weimin, et al., "DFT Test Via Pacing Measurements without VF Induction and Shocking", *PACE*, vol. 23, Abstract No. 235,(Apr. 2000), 1 pg.

Swerdlow, C. D., et al., "Comparative Reproducibility of Defibrillation Threshold and Upper Limit of Vulnerability", *PACE*, 19, (Dec. 1996), pp. 2103-2111.

Swerdlow, Charles, et al., "Determination of the Upper Limit of Vulnerability Using Implantable Cardioverter-Defibrillator Electrograms", *Circulation*, 107, (Jun. 24, 2003), 3028-3033.

Swerdlow, C. D., et al., "Programming of Implantable Cardioverter-Defibrillators on the Basis of the Upper Limit of Vulnerability", *Circulation*, 95 (6), (Mar. 18, 1997), pp. 1497-1504.

Wang, Y., et al., "Analysis of Defibrillation Efficacy from Myocardial Voltage Gradients with Finite Element Modeling", *IEEE Transactions on Biomedical Engineering*, 46 (9), (1999), pp. 1025-1036.

"U.S. Appl. No. 09/808,419, Non-Final Office Action mailed Jul. 16, 2003", 7 pgs.

"U.S. Appl. No. 09/808,419, Non-Final Office Action mailed Sep. 10, 2002", 7 pgs.

"U.S. Appl. No. 09/808,419, Notice of Allowance mailed Jan. 17, 2003", 8 pgs.

"U.S. Appl. No. 09/808,419, Notice of Allowance mailed Feb. 26, 2004", 6 pgs.

"U.S. Appl. No. 10/744,991, Notice of Allowance mailed Sep. 21, 2004", 7 pgs.

"International Application No. PCT/US2008/001637, International Search Report mailed Jul. 9, 2008", 5 pgs.

"International Application Serial No. PCT/US2008/001637, Written Opinion mailed Jul. 9, 2008", 8 pgs.

"European Application Serial No. 06789564.9, Office Action mailed Jul. 15, 2008", 5 pgs.

"U.S. Appl. No. 11/061,315, Final Office Action mailed Apr. 3, 2009", 12 pgs.

"U.S. Appl. No. 11/061,315, Response filed Jan. 22, 2009 Non Final Office Action mailed Jul. 25, 2008", 12 pgs.

"U.S. Appl. No. 06789564.9 Office Action Mailed Aug. 6, 2009", 7 pgs.

"U.S. Appl. No. 11/061,315, Pre-Appeal Brief Request for Review filed Jul. 6, 2009", 5 pgs.

"U.S. Appl. No. 11/695,711, Non-Final Office Action mailed Jan. 29, 2010", 10 pgs.

"European Application No. 08725287.0, Office Action Mailed Feb. 25, 2010", 4 pgs.

"European Application Serial No. 06789564.9, Communication mailed Aug. 6, 2009", 7 pgs.

"European Application Serial No. 06789564.9, Response filed Feb. 15, 2010 to Communication mailed Aug. 6, 2009", 8 pgs.

* cited by examiner

DEFIBRILLATION THRESHOLD PREDICTION METHODS AND SYSTEMS

TECHNICAL FIELD

This patent document pertains generally to defibrillation threshold prediction, and more particularly, but not by way of limitation, to cardiac function management methods and systems.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias uses drug therapy. Drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Such systems are often implanted in the patient and deliver therapy to the heart.

Cardiac rhythm management systems include, among other things, pacemakers, also referred to as pacers. Pacers deliver timed sequences of low energy electric stimuli, called pace pulses, to the heart, such as via an intravascular leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly.

Cardiac rhythm management systems also include defibrillators that are capable of delivering higher energy electric stimuli to the heart. Such defibrillators also include cardioverters, which synchronize the delivery of such stimuli to portions of sensed intrinsic heart activity signals. Defibrillators are often used to treat patients with tachyarrhythmias, that is, hearts that beat too quickly. Such too-fast heart rhythms also cause diminished blood circulation because the heart is not allowed sufficient time to fill with blood before contracting to expel the blood. Such pumping by the heart is inefficient. A defibrillator is capable of delivering a high energy electric stimulus that is sometimes referred to as a defibrillation countershock, also referred to simply as a "shock." The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other implantable or external systems or devices for diagnosing or treating cardiac arrhythmias.

One problem faced by cardiac rhythm management systems is the determination of the threshold energy required, for a particular defibrillation shock waveform, to reliably convert a tachyarrhythmia into a normal heart rhythm. Ventricular and atrial fibrillation are probabilistic phenomena that observe a dose-response relationship with respect to shock strength. The ventricular defibrillation threshold is the smallest amount of energy that can be delivered to the heart to reliably revert ventricular fibrillation to a normal rhythm. Similarly, the atrial defibrillation threshold is the threshold amount of energy that will terminate an atrial fibrillation. Such defibrillation thresholds vary from patient to patient, and may even vary within a patient depending on the placement of the electrodes used to deliver the therapy. In order to ensure the efficacy of such therapy and to maximize the longevity of the battery source of such therapy energy, the defibrillation thresholds must be determined so that the defibrillation energy can be safely set above the threshold value but not at so large of a value so as to waste energy and shorten the usable life of the implanted device.

One technique for determining the defibrillation threshold is to induce the targeted tachyarrhythmia (e.g., ventricular fibrillation), and then apply shocks of varying magnitude to determine the energy needed to convert the arrhythmia into a normal heart rhythm. However, this requires imposing the risks and discomfort associated with both the arrhythmia and the therapy. Electric energy delivered to the heart has the potential to both cause myocardial injury and subject the patient to pain. Moreover, if defibrillation thresholds are being obtained in order to assist the physician in determining optimal lead placement, these disadvantages are compounded as the procedure is repeated for different potential lead placements.

In another technique for determining the defibrillation threshold, referred to as the "upper limit of vulnerability" technique, a patient in a state of normal heart rhythm is shocked during the vulnerable (T-wave) period of the cardiac cycle during which time the heart tissue is undergoing repolarization. Shocks of varying magnitude are applied until fibrillation is induced. Of course, after such fibrillation is induced, the patient must be again shocked in order to interrupt the arrhythmia and reestablish a normal heart rhythm. In this technique, the corresponding fibrillation-inducing shock magnitude is then related to a defibrillation threshold energy using a theoretical model. The upper limit of vulnerability technique also suffers from imposing the risks and discomfort associated with both the arrhythmia and the shock therapy. Moreover, because of the discomfort associated with the fibrillation and countershocks, the patient is typically sedated under general anesthesia, which itself has some additional risk and increased health care cost. For these and other reasons, there is a need to estimate defibrillation thresholds without relying on a defibrillation shock to induce or terminate an actual arrhythmia.

SUMMARY

An example method includes delivering a first nondefibrillating and nonfibrillation-inducing energy at a first internal thoracic location and detecting a first resulting electric signal at a second internal thoracic location in or near a target region of a heart. The first resulting electric signal provides an indication of a first electric field strength in the target region. The method further includes estimating a defibrillation threshold using the first nondefibrillating and nonfibrillation-inducing energy, the first resulting electric signal, and a target electric field strength at the target region of the heart.

Another example method includes delivering a first nondefibrillating and nonfibrillation-inducing energy at a first internal thoracic location and detecting a first resulting electric signal at a second internal thoracic location in or near a target region of a heart. The first resulting electric signal provides an indication of a first electric field strength in the target region. The method further includes estimating a first defibrillation threshold using the first nondefibrillating and nonfibrillation-inducing energy, the first resulting electric signal, and a target electric field strength. The method also includes delivering a second nondefibrillating and nonfibrillation-inducing energy at the first internal thoracic location, detecting a second resulting electric signal at the second internal thoracic location, and determining a change in a defibrillation threshold using the first resulting electric signal and the second resulting electric signal.

Another example method includes delivering a first nondefibrillating and nonfibrillation-inducing energy to a thorax using a first defibrillation configuration, and detecting a first resulting electric signal at an internal thoracic location in or near a target region of a heart. The first resulting electric signal provides an indication of a first electric field strength in the target region. The method also includes delivering a second nondefibrillating and nonfibrillation-inducing energy to the thorax using a second defibrillation configuration and detecting a second resulting electric signal at the internal thoracic location. The second resulting electric signal provides an indication of a second electric field strength in the target region of the heart during delivery of the nondefibrillating and nonfibrillation-inducing energy using the second defibrillation configuration. The method further includes estimating at least one defibrillation threshold using at least one target electric field strength and at least one of the first and second resulting electric signals. In an example, delivering a first nondefibrillating and nonfibrillation-inducing energy to a thorax using a first defibrillation configuration includes delivering the energy through a plurality of electrodes, and delivering a second nondefibrillating and nonfibrillation-inducing energy to the thorax using a second defibrillation configuration includes changing a configuration of the plurality of electrodes and then delivering the energy through the plurality of electrodes. In an example, changing a configuration of the plurality of electrodes includes changing a location of at least one electrode or electrically connecting at least one electrode to at least one other electrode. In another example, delivering a first nondefibrillating and nonfibrillation-inducing energy includes delivering the first nondefibrillating and nonfibrillation-inducing energy using a first electrode configuration, delivering a second nondefibrillating and nonfibrillation-inducing energy includes delivering the second nondefibrillating and nonfibrillation-inducing energy using a second electrode configuration, and estimating at least one defibrillation threshold selecting an electrode configuration that produces a smaller defibrillation threshold for delivery of an antitachyarrhythmia therapy therefrom.

An example system includes an energy module adapted to deliver a nondefibrillating and nonfibrillation-inducing energy using at least a first electrode at a first internal thoracic location, a response signal module adapted to detect a resulting signal using at least a second electrode at a second internal thoracic location in or near a target region of a heart, the responsive signal resulting from the delivery of the energy and providing an indication of an electric field strength at the second internal thoracic location, and a controller communicatively coupled to the energy module and the response signal module, the controller adapted to estimate a defibrillation threshold using the nondefibrillating and nonfibrillation-inducing energy and the resulting signal. In an example, the controller is adapted to compare a detected resulting signal with a previous detected resulting signal to detect a change in the resulting signal indicative of a defibrillation threshold change, or to compare an estimated defibrillation threshold to a previously estimated defibrillation threshold to detect a change in the defibrillation threshold. In an example, the controller is adapted to deliver a notification if an changed defibrillation threshold is detected or to increase an energy level of an antitachyarrhythmia therapy if an increased defibrillation threshold is detected.

DETAILED DESCRIPTION

Figure 1:
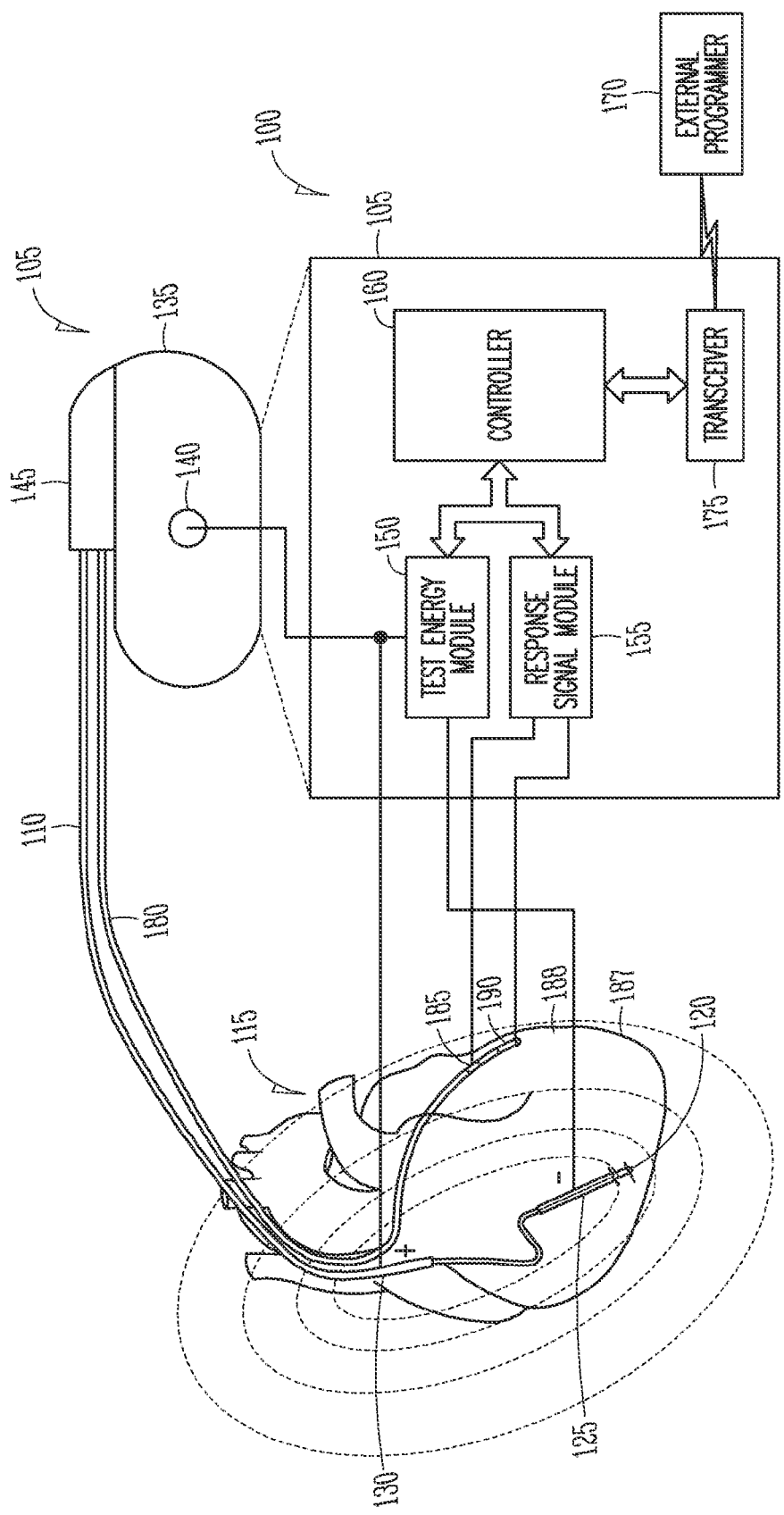
FIG. 1 is a schematic/block diagram illustrating portions of an example cardiac rhythm management system and portions of an environment of use.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electric changes may be made without departing from the scope of the present invention. The following detailed description is, therefore, not to be taken in a limiting sense, and the scope of the present invention is defined by the appended claims and their equivalents. The term "and/or" refers to a nonexclusive "or" (i.e., "A and/or B" includes both "A and B" as well as "A or B").

The present methods and apparatus will be described in applications involving implantable medical devices including, but not limited to, implantable cardiac function management systems such as pacemakers, cardioverter/defibrillators, pacer/defibrillators, biventricular or other multi-site coordination or resynchronization devices, and drug delivery systems for managing cardiac rhythm. However, it is understood that the present methods and apparatus may be employed in unimplanted devices, including, but not limited to, external pacemakers, cardioverter/defibrillators, pacer/defibrillators, biventricular or other multi-site coordination or resynchronization devices, monitors, programmers and recorders.

Overview

An estimated defibrillation threshold energy is determined based upon a desired electric field strength in a target region of the heart. In an example, an energy is delivered at a first internal thoracic location, such as a location in, on, or near the heart. The delivered energy is preferably, but not necessarily, a nondefibrillating and nonfibrillation-inducing energy. A resulting electric signal is detected at a second internal thoracic location in or near the target region of the heart. In an example, the energy is delivered to the right side of the heart, and the target region is in, on, or near the left apical region of the heart and/or a left free lateral wall. The resulting electric signal is used to estimate the defibrillation threshold energy required to create the desired electric field strength in the target region. In an example, the estimated defibrillation threshold energy is determined using a ratio of the desired (or "target") electric field strength (e.g. 5 volts/cm) to the electric field strength produced by the delivered energy. In an example, a ventricular and/or atrial defibrillation threshold is determined. In an example, actual measurement of a resulting electric field in or near the target region avoids reliance on fluoroscopic distance measurement and electric field modeling computations.

In an example, defibrillation thresholds are determined for multiple shock electrode configurations, allowing for selection of a low-threshold configuration that can be used to conserve energy and prolong battery life.

An increase in defibrillation threshold may be indicative of hypertrophy, ventricle dilation, ischemia or myocardial infarction, scar tissue, or lead dislodgement. In an example, when an increased defibrillation threshold is detected, a defibrillation therapy energy is increased, or a notification such as a warning is delivered.

The present techniques typically reduce risks to a patient by permitting defibrillation threshold determination without inducing fibrillation or delivering a fibrillation-inducing shock energy. For example, using the present techniques, a very sick patient for whom a doctor hesitates to do a standard defibrillating test to determine a defibrillation threshold could be fitted with a defibrillator while avoiding delivery of a defibrillating shock to test the patient's defibrillation threshold. In another example, patients are screened using the present techniques to identify patients suitable for defibrillation.

EXAMPLE SYSTEMS

FIG. 1 is a schematic/block diagram illustrating generally, by way of example, and not by way of limitation, one embodiment of portions of a cardiac rhythm management system 100 and portions of an environment in which the present system 100 and associated techniques are used. In this example, the system 100 includes, among other things, cardiac rhythm management device 105 and leadwires ("leads") 110, 180 for communicating signals between device 105 and a portion of a living organism, such as heart 115. Embodiments of device 105 include, but are not limited to, bradycardia and antitachycardia pacemakers, cardioverters, defibrillators, combination pacemaker/defibrillators, drug delivery devices, and any other implantable or external cardiac rhythm management apparatus capable of diagnosing or providing therapy to heart 115.

FIG. 1 illustrates, in an exploded view block diagram form, portions of an example device 105. In an example, the illustrated device 105 is coupled to leads 110 and 180 that extend toward the heart; however, the illustrated connection lines associated with the exploded view are illustrative only. In FIG. 1, test energy module 150 generates an energy that is delivered by electrodes, such as two or more of electrodes 125, 130, and/or 140, at an internal thoracic location, such as a location in, on, or around the heart. In an example, electrodes 125, 130, and 140 all act as separate electrodes. Alternatively, two or more electrodes are electrically commonly connected. In an example, SVC electrode 130 is electrically connected in common with housing electrode 140. In an example, the test energy module 150 is adapted to deliver the energy at a specified time, such as at the end of systole when the intrinsic electric activity in the heart is relatively quiet.

A defibrillation threshold energy can be determined via response signal module 155, which is connected for example to electrodes 185, 190 on lead 180. In an example, electrodes 185, 190 are located at a second internal thoracic location, which is optionally in, or near, a target region of a heart. Electrodes 185, 190 detect a responsive electrical signal resulting from the delivery of the energy. The responsive electrical signal provides an indication of an electric field strength at the second internal thoracic location. In an example, the test energy module 150 is adapted to deliver a current and the response signal module 155 is adapted to detect a responsive voltage or a responsive current density. From the responsive detected signal(s), a defibrillation threshold is computed, for example, by a defibrillation threshold estimation module in controller 160. Controller 160 is in device 105, or in external programmer 170, which is communicatively coupled to a transmitter or receiver in device 105, such as transceiver 175. The defibrillation threshold estimation module is typically implemented as a sequence of acts carried out on a microprocessor or other microsequencer, in analog, digital, or mixed-signal hardware, or in any suitable hardware and/or software configuration.

In an example, the controller 160 estimates a defibrillation threshold energy that when delivered to the first internal thoracic location creates an electric field strength in the target region of the heart that meets or exceeds a target electric field strength. In a further example, the controller 160 compares an estimated defibrillation threshold to a previously estimated defibrillation threshold to detect a change in the defibrillation threshold, if any. In an example, the controller 160 is adapted to increase an energy level of an antitachyarrhythmia therapy if an increased defibrillation threshold is detected, and/or deliver a notification (e.g., a warning) if an increased defibrillation threshold is detected. In an example, a notification is delivered if the defibrillation threshold increases by a specified amount in a specified amount of time. In an illustrative example, if the defibrillation threshold increases by at least 20% over 3 months, a notification is delivered. In another example, a notification is delivered if the defibrillation threshold increases by a specified amount, without regard to the amount of time over which the increase occurs. In an example, the controller is configured to switch to a (different) second electrode configuration, estimate a second defibrillation threshold for at least a second electrode configuration, compare estimated defibrillation thresholds for at least two electrode configurations, and optionally select a particular electrode configuration using the estimated defibrillation thresholds, so that the selected electrode configuration can be used to then deliver antiarrhythmia therapy.

In the example shown in FIG. 1, lead 110 includes multiple electrodes, and typically includes individual conductors for independently communicating an electrical signal from each electrode to device 105. In one embodiment, these electrodes include a right ventricular (RV) tip-type electrode 120 at the distal end of lead 110. In one example, electrode 120 has a macroscopic surface area that is approximately between 1 mm$^2$ and 20 mm$^2$, inclusive. RV tip electrode 120 is sized and shaped to be positioned in the right ventricle, such as at or near its apex or at any other suitable location. RV shock electrode 125 is typically located on the lead at a known or estimated distance, d1, from RV tip electrode 120, as measured from the edges of these electrodes. RV shock electrode 125 is typically located in the right ventricle or at any other suitable location. In one embodiment, RV shock electrode 125 is a coil-type electrode having a macroscopic surface area that is approximately between 2 cm$^2$ and 20 cm$^2$, inclusive. Superior vena cava (SVC) electrode 130 is typically located in a portion of the superior vena cava, the right atrium, or both, or at any other suitable location. In one embodiment, SVC electrode 130 is a coil-type electrode having a macroscopic surface area that is approximately between 2 cm$^2$ and 20 cm$^2$, inclusive. Although RV tip electrode 120, RV shock electrode 125, and SVC electrode 130 are particularly described above with respect to structural characteristics and locations for disposition, it is understood that these electrodes may take the form of any of the various cardiac or like electrodes known in the art (e.g., epicardial patch electrodes) and may be positioned elsewhere for association with heart 115 or other tissue.

The system 100 also typically includes second and third electrodes 185, 190 located in, on, or near the left side of the heart. In an example, the second electrode 185 is located at a portion of the heart that is expected to experience a relatively lesser effect of the defibrillation energy, such as at or close to the peripheral portion, apical region, and/or free lateral wall of the left ventricle, at which a target electric field magnitude (e.g., 5 volts/cm) is desired during defibrillation. In one embodiment, this electrode 185 is introduced into the left ventricular periphery (e.g., coronary sinus and/or great cardiac vein or the like) by a transvascular lead 180 through the right atrium and coronary sinus.

In an example, the lead 180 and/or electrodes 185, 190 are sized and shaped for implantation in the great cardiac vein or elsewhere in or on the left region of the heart, such as in or on a left apical region or left free lateral wall. In another embodiment, electrode 185 is a patch-type defibrillation electrode disposed on the exterior portion of the left ventricle. The lead 180 may also include additional electrodes.

Referring again to FIG. 1, in one embodiment, device 105 includes a hermetically sealed housing 135, formed from a conductive metal, such as titanium, and implanted within a patient such as within the pectoral or abdominal regions. In one example, housing 135 (also referred to as a "case" or "can") forms a "case" or "can" or "housing" electrode 140. As understood by one of ordinary skill in the art, housing electrode 140, although not located in the heart, is associated with the heart for providing what is sometimes referred to as "unipolar" sensing or pacing or defibrillation therapy. In one embodiment, a header 145 is mounted on housing 135, such as for receiving lead 110. Header 145 is formed of an insulative material, such as molded plastic. Header 145 also includes at least one receptacle, such as for receiving lead 110 and electrically coupling conductors of lead 110 to device 105. Header 145 may also include one or more additional electrodes.

In an example, fibrillation is treated by delivering a shock between RV shock electrode 125 and SVC electrode 130. In another example, ventricular fibrillation is treated by delivering a defibrillation shock between RV shock electrode 125 and the commonly connected combination of SVC electrode 130 and housing electrode 140. It is understood that these electrodes could be differently configured, and that more or fewer electrodes could be used.

EXAMPLE METHODS AND SYSTEM CONFIGURATIONS

In various examples, a system of electrodes and at least one processor, such as the system shown in FIG. 1, is used to deliver a nondefibrillating and non-fibrillation inducing energy, detect a responsive electric signal, and determine a defibrillation threshold therefrom.

Figure 2A:
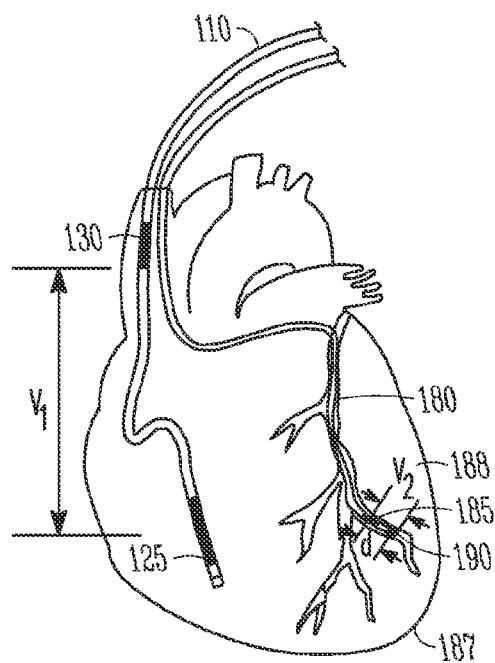
FIG. 2A is an illustration of example configuration of electrodes and a heart.
Figure 7:
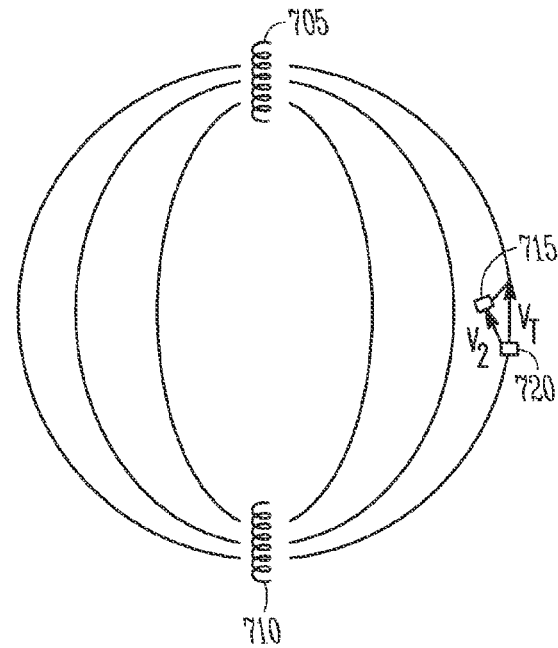
FIG. 7 is a schematic illustration of an electric field generated by defibrillation electrodes and a projection of an electric field vector on a vector defined by sensing electrodes.

Referring now to FIG. 2A, in an example, electrodes 185 and 190 are positioned a known (or estimated) distance (d) apart on lead 180 inserted into a vessel, such as the great cardiac vein. In an example, electrode 185 is a ring electrode and electrode 190 is a tip electrode. When a first voltage $V_1$ is delivered, for example using RV shock electrode 125 and SVC electrode 130, a second voltage $V_2$ is detectable using electrodes 185 and 190. The voltage $V_2$ provides an indication of the strength of the electric field in a target region around electrodes 185 and 190. A field strength (potential gradient) can be determined from the voltage $V_2$ and the distance d between the electrodes 185, 190. Dividing $V_2$ by the distance d provides a field strength, which is the projection of the potential gradient space vector on the vector defined by the electrodes. A defibrillation threshold energy is estimated using the voltages $V_1$ and $V_2$. The estimated defibrillation threshold energy typically yields a somewhat conservative estimate (i.e., high), because the potential gradient $V_2/d$ is usually only a fraction of the actual potential gradient space vector. For example, in FIG. 7, when an energy is delivered using defibrillation electrodes 705, 710, the voltage $V_2$ across sensing electrodes 715, 720 (which are space a distance d apart) is the projection of the total voltage gradient $V_T$ on the vector defined by the sensing electrodes.

In an example, the estimated defibrillation threshold energy is selected to create an electric field strength in the target region of the heart that meets or exceeds a target electric field strength. In an example, the target electric field strength is 5 volts/cm. In another example, the target electric field strength is around 1-2 volts/cm. In an example, the target electric field strength is selected using a target voltage gradient that includes a safety margin.

In an example, a defibrillation threshold voltage is determined by multiplying $V_1$ by a ratio of a target potential gradient (e.g. 5 volts/cm) and a measured voltage gradient ($\Delta V_L$):

$$V_{DFT} = V_1 \frac{5(\text{V/cm})}{\Delta V_L(\text{V/cm})}$$

A defibrillation threshold energy EDFT can be determined from the defibrillation threshold voltage and a defibrillation energy storage capacitance (C) associated with the device that delivers the therapy:

$$E_{DFT} = \frac{CV_{DFT}^2}{2}$$

It is understood that the defibrillation threshold energy can be determined or expressed in terms of energy units, such as Joules, or alternatively in terms of the charged voltage of a capacitor, from which an energy therapy is delivered.

In an example, the target region is at or near a location where a relatively low electric field is expected for a given configuration of the electrodes that deliver the energy. For example, where the energy is delivered at the right side of the heart as shown in FIG. 1, the left apical region 187 of the heart or the left free lateral wall 188 is expected to experience a relatively low electric field, and in some instances the lowest electric field in the heart. Thus, it can be expected that an energy that generates a sufficient electric field in the target region to achieve defibrillation (e.g. 5 volts/cm) will generate an equal or greater electric field in most or all of the other locations in the heart.

Figure 2B:
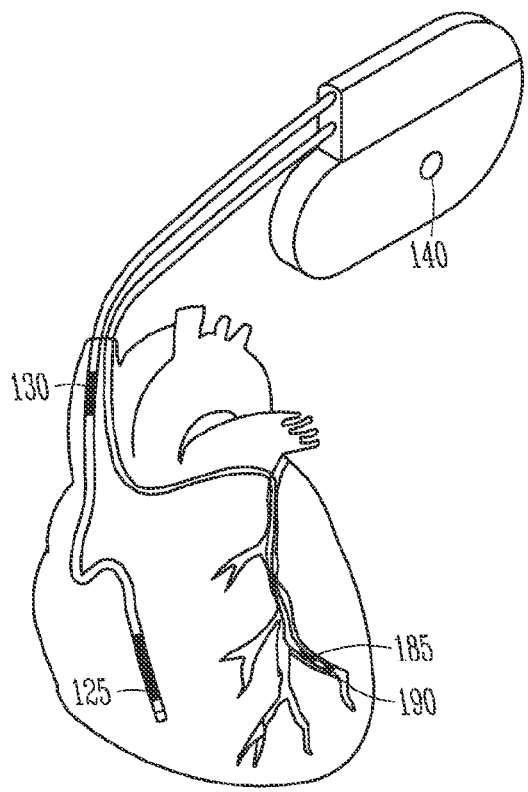
FIG. 2B is an illustration of an example system including electrodes in and/or on a heart and a medical device including at least one electrode on the device.

Referring now to FIGS. 2A and 2B, in an example, a nondefibrillating and nonfibrillation-inducing energy is delivered and/or sensed using two different electric configurations of the electrodes. In an example, the different electrode configurations provide different vectors for delivering such energy or sensing a responsive electric signal. For example, FIG. 2B shows an electric configuration different from the configuration shown in FIG. 2A. In FIG. 2B, electrode 130 is electrically connected to the electrode 140 on the housing 135. In an example, a first nondefibrillating and nonfibrillation-inducing energy is delivered using the electrode configuration shown in FIG. 2A, where electrode 135 is not electrically connected to electrode 140, and a first resulting electric signal is detected. A second nondefibrillating and nonfibriulation-inducing energy is delivered using the electrode configuration shown in FIG. 2B, and a second resulting electric signal is detected. The first and second resulting electric signals are each evaluated to determine a corresponding defibrillation threshold energy. In an example, an electrode configuration having a lower defibrillation threshold energy is selected.

Figure 2C:
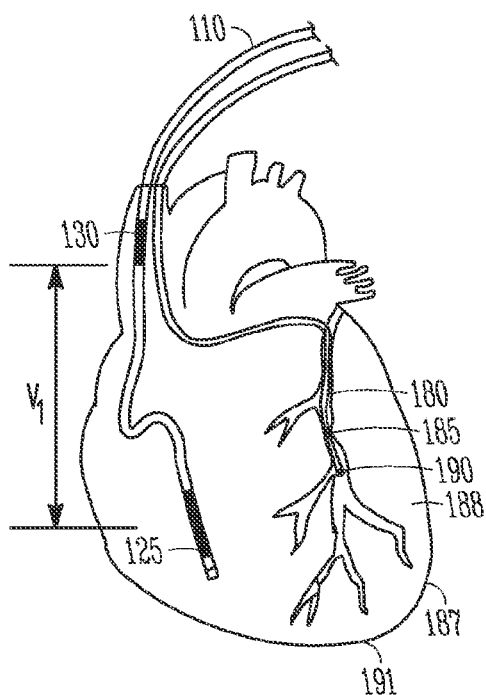
FIG. 2C is an illustration of the electrodes of FIG. 2A, with some of the electrodes in a different position.

Referring now to FIGS. 2A and 2C, in an example, a defibrillation threshold is determined using two or more resulting electrical signals corresponding to two or more sensor electrode configurations. FIG. 2C shows the same components as FIG. 2A but in a different configuration. Lead 180 and electrodes 185 and 190 are positioned further from the apex 191 of the heart in FIG. 2C than in FIG. 2A. In an example, a nondefibrillating and nonfibrillation-inducing energy is delivered with the electrodes in the configuration shown in FIG. 2C, and then the lead 180 is inserted further into a blood vessel on the heart until the electrodes are positioned in the configuration shown in FIG. 2A, at which time another nondefibrillating and nonfibrillation-inducing energy is delivered. Resulting electrical signals are detected using both lead configurations. A defibrillation threshold energy is estimated using one or both of the corresponding resulting electrical signals. In an example, more than two configurations of lead 180 are used. In another example, resulting electrical signals are detected occasionally, periodically, or continuously as lead 180 is inserted into a vessel or into the heart. Electrical signals at different locations can be used, for example, to assess electric fields at different locations of the left ventricle free wall or the apical region and find the minimum electric field in the target region. In another example, the resulting electric field in different directions is used to estimate an electric field strength projected in the strongest direction. In an example, lead 110 is maintained in a fixed position as lead 180 is moved.

Referring now to FIGS. 2A and 2C, in an example, a defibrillation threshold is determined using two or more resulting electrical signals corresponding to two or more sensor electrode configurations. FIG. 2C shows the same components as FIG. 2A but in a different configuration: lead 180 and electrodes 185 and 190 are positioned further from the apex 191 of the heart in FIG. 2C than in FIG. 2A. In an example, a nondefibrillating and nonfibrillation-inducing energy is delivered with the electrodes in the configuration shown in FIG. 2C, and then the lead 180 is inserted further into a blood vessel on the heart until the electrodes are positioned in the configuration shown in FIG. 2A, at which time another nondefibrillating and nonfibrillation-inducing energy is delivered. Resulting electrical signals are detected using both lead configurations. A defibrillation threshold energy is estimated using one or both of the corresponding resulting electrical signals. In an example, more than two configurations of lead 180 are used. In another example, resulting electrical signals are detected occasionally, periodically, or continuously as lead 180 is inserted into a vessel or into the heart. Electrical signals at different locations can be used, for example, to assess electric fields at different locations of the left ventricle free wall or the apical region and find the minimum electric field in the target region. In another example, the resulting electric field in different directions is used to estimate an electric field strength projected in the strongest direction. In an example, lead 110 is maintained in a fixed position as lead 180 is moved.

In another example, two or more configurations of lead 110 are evaluated using resulting electrical signals detected using electrodes on lead 180.

Figure 2D:
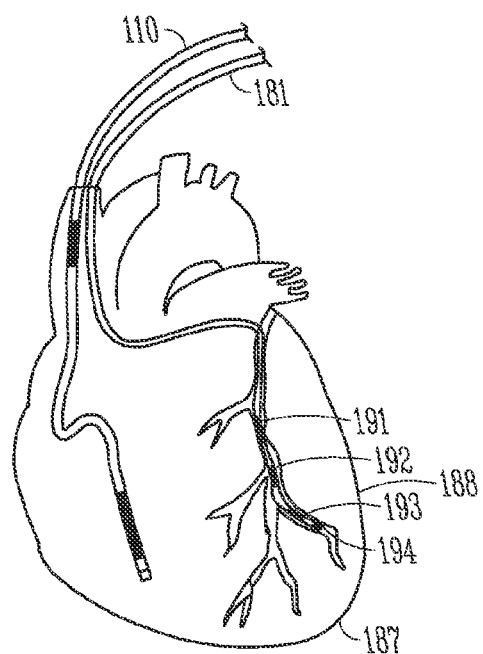
FIG. 2D is an illustration of a lead having four electrodes.

Referring now to FIG. 2D, in another example, a multipolar lead is used to detect the first resulting electrical signal. FIG. 2D shows a lead 181 and electrodes 191, 192, 193, and 194. In an example, a portion of the lead including some or all of the electrodes 191, 192, 193, 194 has a nonlinear shape, such as a two-dimensional (2-D) or three-dimensional (3-D) shape, such as a serpentine or helix, respectively. In an example, the electrodes 191, 192, 193, 194 are all used to detect the first resulting electrical signal. In an example, the electrodes are located in the left apical region 187, and/or in a left lateral free wall 188. In an example, a two-part process is used. First, different directional potential gradients associated with the same particular region of the heart are measured. A representative potential gradient is selected for that region (e.g., an average gradient or, more typically, a maximum gradient). Second, after representative potential gradients have been determined for various regions of the heart, then that particular region having a minimum potential gradient is then used to estimate the defibrillation threshold energy. For example, a defibrillation threshold energy is selected to provide a specified electric field between electrodes at a region of the heart having a minimum detected voltage difference, on the assumption that the electrodes represent a region of the heart having a lowest electric field.

The electrodes used to detect a resulting electrical signal are not necessarily located on the same lead. In an example, an electrode at a distal end of lead 110 is in combination with an electrode on lead 180 to detect a resulting electrical signal. In an example, lead 110 is extended around to the left side of the heart and shock electrode 125 is located far enough from the distal end of the lead to allow for useful detection at the distal end.

Similarly, the electrodes used to deliver a first nondefibrillating and nonfibrillation-inducing energy are not necessarily on the same lead. For example, a defibrillation electrode could be placed on lead 180 or 181, or on another separate lead, and used in combination with electrode 125 or 130 on lead 110 to deliver an energy. It should be noted that when the defibrillation electrode configuration is changed, the target region may also change.

It is also understood that the leads can extend in, on, or near the heart. In an example, lead 180 extends near the heart and the electrodes 185, 190 are located outside the target region of the heart. The lead 110 can also be positioned so that the electrodes 125, 130 are positioned in, on, or near the heart. In another example, the electrodes 125, 130 for delivering the nondefibrillating and nonfibrillation-inducing energy are implanted subcutaneously. In an example, far-field sensing is used to detect the resulting electrical signal.

It is also understood that, while the figures generally depict delivery of an energy to a right side of the heart and detection of a resulting electrical signal in, on, or near the left side of the heart, the methods and systems described herein can be used in other configurations. For example, in alternative configurations, energy is delivered to the left side of the heart, delivered by subcutaneous electrodes, or delivered to the coronary sinus, or delivered through epicardial electrodes.

Figure 3:
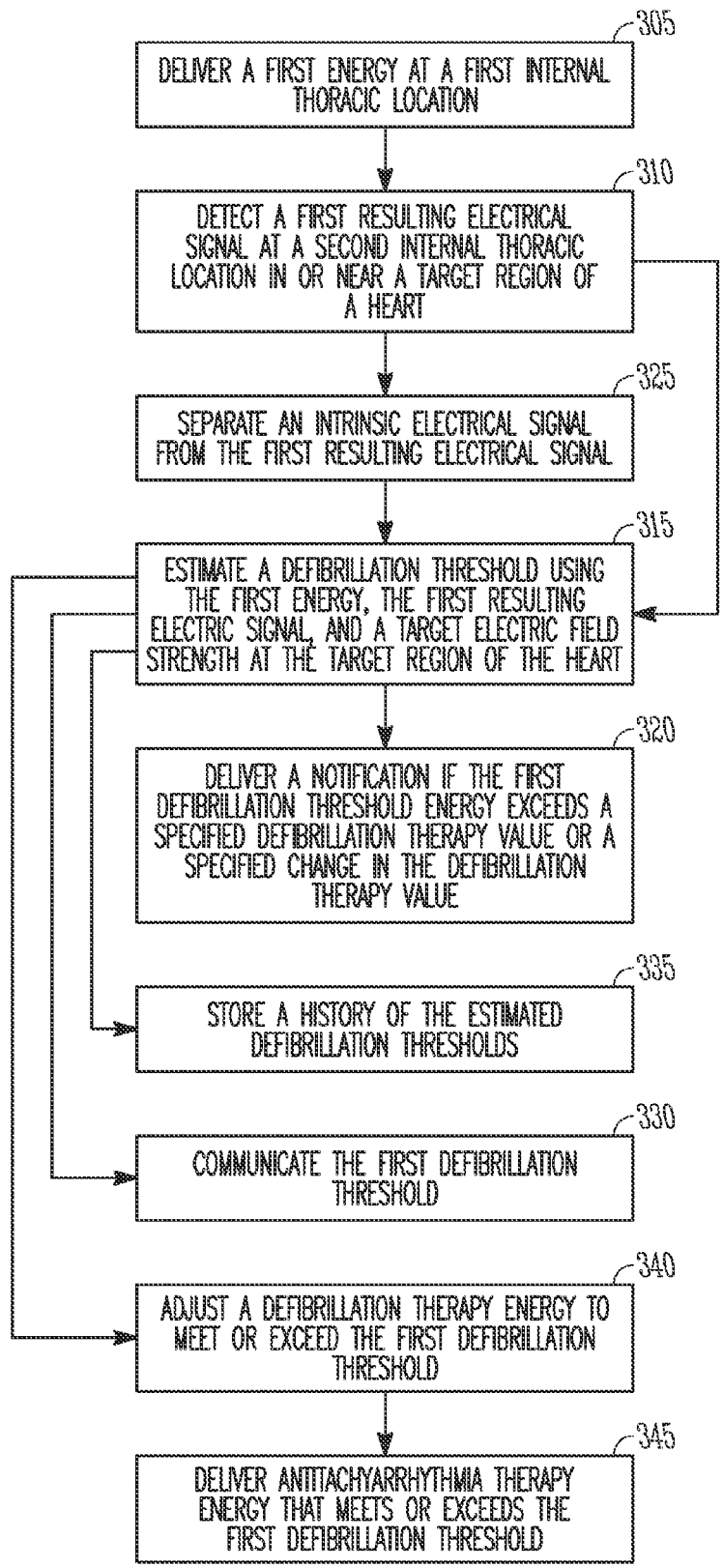
FIG. 3 is a flow chart illustrating an example method that includes delivering an energy, detecting a resulting electric signal in or near a target region of a heart, and estimating a defibrillation threshold.

FIG. 3 is a flowchart that schematically illustrates an example of a method. At 305, a first energy is delivered at a first internal thoracic location. In an example, the first energy is nondefibrillating and nonfibrillation-inducing. In an example, the energy is delivered at a location in and/or near the heart. In an example, the energy is delivered at a subcutaneous location. In an example, the energy is non-stimulating. In an example, the energy is below a patient's pain threshold and/or below a patient's perception threshold. In an example, the energy is delivered during a specified portion of a cardiac cycle, such as at the end of systole.

At 310, a first resulting electrical signal is detected at a second internal thoracic location in or near a target region of a heart. In an example, the second internal thoracic location is in the target region. In an example, the energy is delivered at a location in or near a right region of the heart, such as in the right ventricle or the superior vena cave, and the first resulting electrical signal is detected at a location in or near a left region of the heart, such as in or near a left apical region, and/or in or near a left free lateral wall. In an example, delivering the energy includes delivering a current and detecting the resulting signal includes detecting a voltage between two electrodes or a current density. In an example, the first resulting electrical signal is detected through a lead inserted into vasculature on or in the heart, such as vasculature on the left side of the heart. In an example, the lead is chronically implanted. In an example, the first resulting electric signal is detected through electrodes in a bipolar lead or multipolar lead, which is optionally located in the left side of the heart. In an example, the first resulting electrical signal is detected using a guide wire, for example by detecting a voltage difference between an electrode on or of the guide wire and an electrode on the lead. In an example, a distance between a distal end of the guide wire and an electrode on the lead is estimated using one or more features or markings at the proximal end of the guide wire. In an example, a position of a marking at the proximal end of the guide wire is recorded and correlated to a position of the distal end of the guide wire. When the guide is advanced, the displacement of the distal end of the guide wire is estimated using the marking at the proximal end.

In another example, a lead is temporarily inserted in or around the heart and used to detect resulting electrical heart signals. In an example, a temporary mapping catheter is inserted in or around the heart. In an example, the temporary mapping catheter has a multiplicity of electrodes (e.g. 16 or 24 electrodes) that detect resulting electrical signals at locations in or around the heart. In an example, each electrode is coupled to a separate conductor (e.g. the mapping lead has 16 conductors and 16 electrodes.) In another example, the lead assembly includes switching capacity (e.g. a multiplexor) so that a resulting electrical signal can be detected using a selected combination of selected electrodes. In an example, one or more of the resulting electrical signals are used to estimate a defibrillation threshold.

Returning to FIG. 3, at 315, a defibrillation threshold energy is estimated. In an example, the defibrillation threshold includes an energy, a voltage, a current and/or a duration. The defibrillation threshold energy when delivered to the first internal thoracic location creates an electric field strength in the target region of the heart that meets or exceeds a target electric field strength. In an example, detecting the resulting signal includes detecting at least one voltage difference between (or among) electrodes, and the estimating includes determining the first electric field strength from the at least one voltage difference and a known configuration of the electrodes. In an example, the estimating further includes dividing the target defibrillating electric field strength by the first electric field strength to determine a defibrillation scaling factor; and multiplying the first nondefibrillating and non-fibrillation-inducing voltage or current by the defibrillation scaling factor to determine the defibrillation threshold voltage or current. In an example, estimating the defibrillation threshold energy includes combining fields from three or more electrodes. Optionally, at 325, before a defibrillation threshold is estimated, at least one intrinsic electrical signal is separated from the first resulting electrical signal. In an example, a post-processing technique is used to subtract out electrical noise. In an example, a remainder of the detected resulting electrical signal is substantially attributable to the delivery of the energy at the first internal thoracic location. In an example, the remainder of the resulting electrical signal is used to estimate the defibrillation threshold. In an example, a blind source separation technique is used to separate at least one intrinsic electric signal from the detected resulting electric signal. Blind source separation techniques are described in copending U.S. patent application Ser. No. 10/876,008, filed Jun. 24, 2004, entitled "Automatic Orientation Determination for ECG Measurements Using Multiple Electrodes," which is incorporated herein by reference in its entirety.

Referring again to FIG. 3, at 320 a notification is delivered if the estimated defibrillation threshold energy meets or exceeds a specified value or a specified change in value. In an example, a notification is received by a patient, for example by detecting an audible sound such as a beep. In another example, a notification is received by a physician, for example by using an external device that communicates with an implanted device wirelessly or otherwise. In yet another example, a notification is received by a physician via Internet or other communication over a communications network. In an example, a notification is delivered if the estimated defibrillation threshold energy meets or exceeds a prescribed defibrillation energy value by 20%. At 330, the defibrillation threshold energy is communicated, for example to an external programmer. At 335, a history of estimated defibrillation threshold energies is stored. Storing a history of estimated defibrillation threshold energies allows for monitoring of a physiological condition, for example. It also allows for monitoring of lead position change or dislodgement. A defibrillation threshold can change over time, for example due to myocardial infarction, cardiac remodeling, medication changes, hypertrophy, posture change, or lead dislodgement. At 340, a defibrillation therapy is adjusted to meet or exceed the defibrillation threshold energy.

At 345, a defibrillation therapy energy meeting or exceeding the defibrillation threshold is delivered. In an example, the antitachyarrhythmia therapy is delivered through an electrode that was also used to deliver the energy from which the defibrillation threshold was determined. In an example, the antitachyarrhythmia therapy includes a defibrillation shock delivered at an energy meeting or exceeding the estimated defibrillation threshold. In an example, an arrhythmia such as a tachyarrhythmia is detected or declared, a nondefibrillating and nonfibrillation-inducing energy is delivered, from which a defibrillation threshold is determined, and then an antitachyarrhythmia therapy having an energy meeting or exceeding the defibrillation threshold is delivered.

Figure 4:
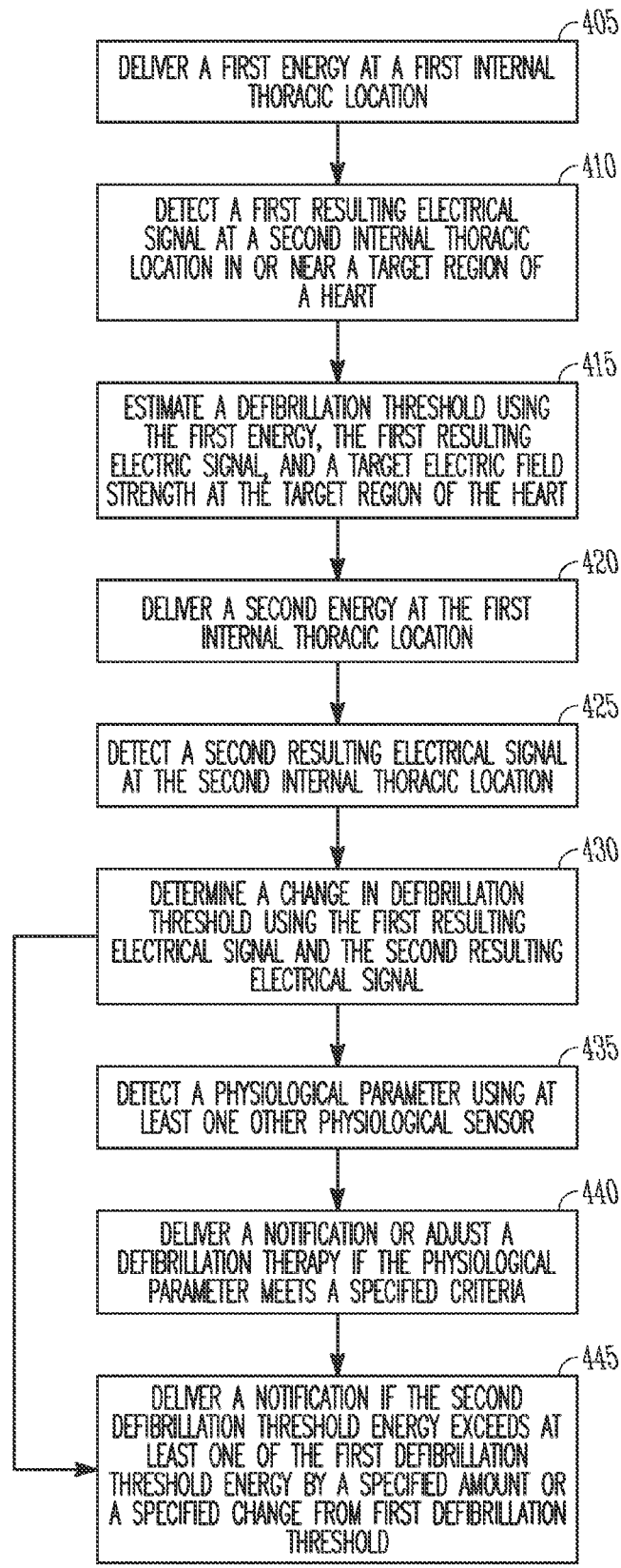
FIG. 4 is a flow chart illustrating an example method that includes delivering first and second energies, detecting respective first and second resulting electric signals, and determining a change in a defibrillation threshold.

Turning now to the flow chart provided in FIG. 4, a first energy is delivered at 405 at a first internal thoracic location, a first resulting electrical signal is detected at 410, and a first defibrillation threshold is estimated at 415. At 420, a second energy is delivered to the first internal thoracic location. At 425, a second resulting electrical signal is detected.

At 430, a change in defibrillation threshold is determined using the first resulting electrical signal and the second resulting electrical signal. In an example, a first electric field strength determined from the first resulting electrical signal is compared with a second electric field strength determined from the second resulting electrical signal. In an example, a second defibrillation threshold energy is estimated for the target region of the heart using the indication of a second electric field strength and the second energy, and the second estimated defibrillation threshold is compared to the first defibrillation threshold.

Returning to FIG. 4, at 445, a notification is delivered if the second defibrillation threshold energy exceeds the first defibrillation threshold energy by a specified amount. In an example, a notification is delivered if the second defibrillation threshold exceeds the first defibrillation threshold by a specified amount over a specified amount of time. Optionally, at 435, data from at least one other sensor is analyzed. In an example, the data from the other sensor is used to confirm a change in a defibrillation threshold or characterize a physiologic condition or change. In an example, such information is used to assess whether a notification is delivered or a defibrillation therapy should be altered. Factors such as posture, for example, can affect a defibrillation threshold, and defibrillation thresholds affected by such factors may not necessarily warrant delivery of a notification. At 440, a notification is delivered or a defibrillation therapy is adjusted if the physiological parameter detected at 435 meets a specified criteria.

Figure 5:
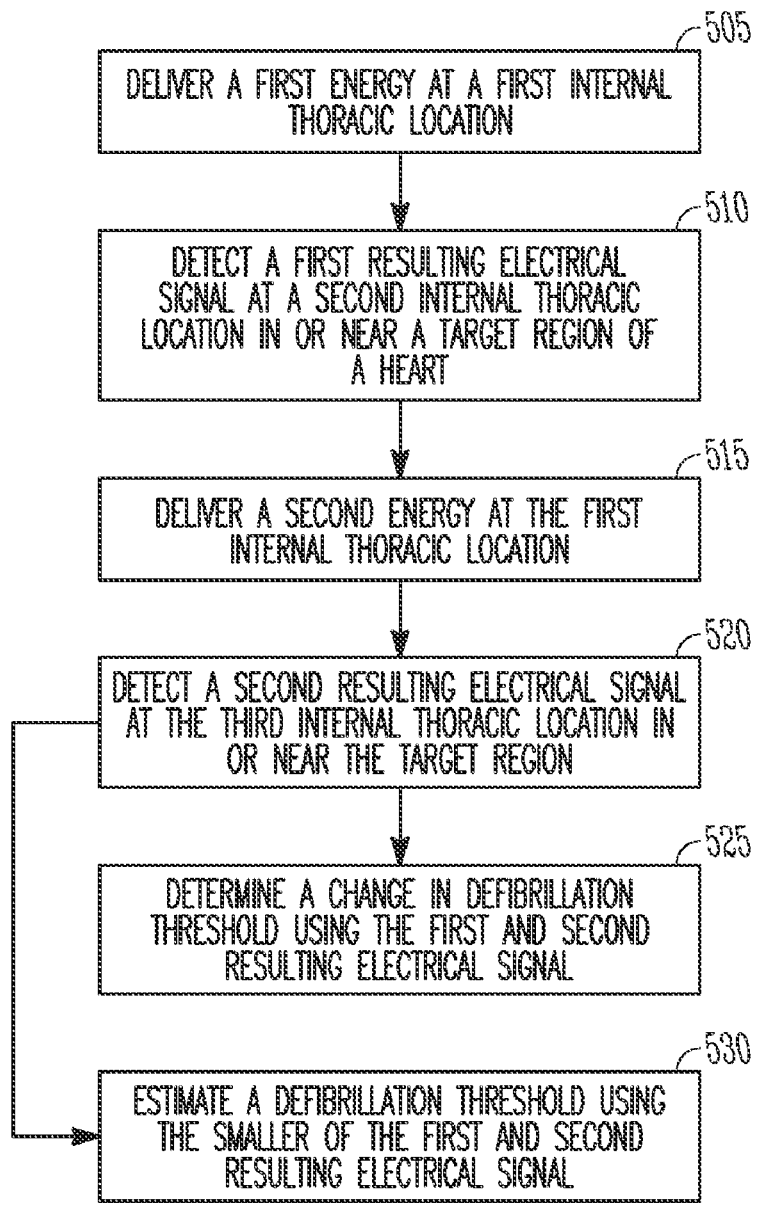
FIG. 5 is a flow chart illustrating an example method that includes delivering first and second energies and detecting respective first and second resulting electric signals at different locations.

Referring now to FIG. 5, at 505 a first nondefibrillating and nonfibrillation-inducing energy is delivered at a first internal thoracic location. At 510, a first resulting electrical signal is detected at a second internal thoracic location in or near a target region of a heart. In an example, the first resulting electrical signal is detected using one or more pacing/sensing electrodes. In another example, the first resulting electrical signal is detected using a guide wire and an intravascular lead. At 515, a second nondefibrillating and nonfibrillation-inducing energy is detected at the first internal thoracic region. At 520, a second resulting electrical signal is detected at a third internal thoracic location in or near the target region. In an example, the second internal thoracic location and third internal thoracic location are locations of electrodes on a lead.

In an example, detecting a first electrical signal includes detecting an electrical signal at a first position on a lead inserted into a coronary vein in the left side of the heart, and detecting a second resulting electrical signal includes detecting an electrical signal through the lead in a second position in a coronary vein in the left side of the heart. FIGS. 2A and 2C, for example, show a lead at two positions in a coronary vein. In an example, detecting an electrical signal through a lead in a coronary vein in the left side of the heart includes detecting at least two voltage differences between electrodes on the lead. In an example, the lead includes a multi-polar lead, as shown in FIG. 2D for example. In an example, detecting an electrical signal through a lead in a coronary vein in the left side of the heart includes detecting an electrical signal through electrodes on a portion of the lead that extends has a two-dimension path or three-dimensional bias, such as a helical bias, for example. In an example, positioning electrodes on a portion of a lead that has 3-D bias promotes electric contact with tissue. In an example, positioning electrodes on a lead that follows a 3-D path allows for positioning of the electrodes at a desired contact location within a vessel, for example to avoid stimulating anatomy such as a nerve.

Returning to FIG. 5, at 525, both the first resulting electrical signal and the second resulting electrical signal are combined and the combination is used to estimate a defibrillation threshold. In an example, an average of the first resulting electrical signal and the second resulting electrical signal is used to determine a defibrillation threshold. In an example, the average is a weighted average. In an example, multiple measurements (e.g. 10's or 100's of resulting electrical signals) are used to estimate a defibrillation threshold. In an example, a median or a specified standard deviation from a mean is used to estimate a defibrillation threshold. In an example, space vector synthesis is used to estimate a defibrillation threshold. Blind source separation may also be used to estimate a defibrillation threshold. Alternatively, at 530, the smaller of the first and second resulting electrical signals is used to determine a defibrillation threshold. In an example, a resulting electrical signal is detected at various locations in, on, or near the heart to identify a region having a lowest value of a potential gradient. Determining a defibrillation threshold using the lowest potential gradient ensures that the location where the lowest potential gradient was observed will reach a sufficient defibrillating potential gradient when a therapeutic energy is delivered.

Figure 6:
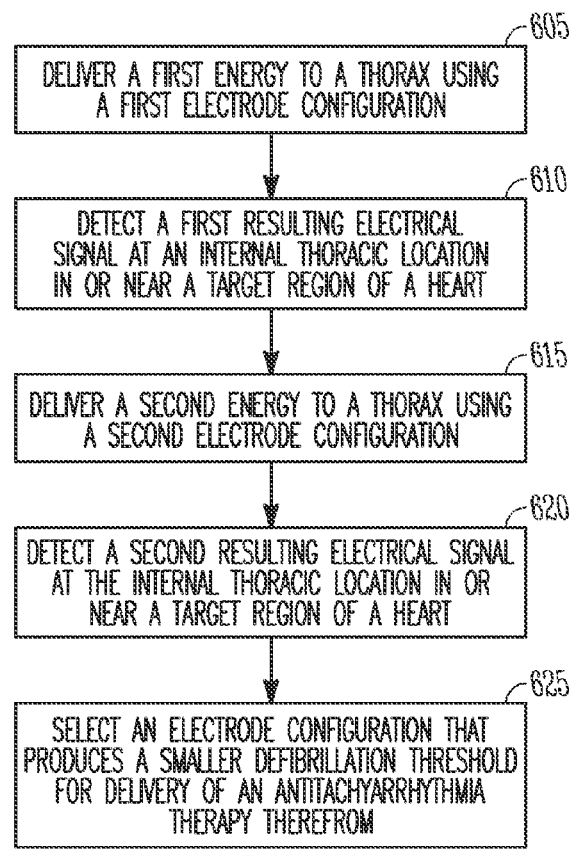
FIG. 6 is a flow chart illustrating an example method that includes delivering energy using different electrode configurations.

Referring now to FIG. 6, at 605, a nondefibrillating and nonfibrillation-inducing energy is delivered to a thorax using a first electrode configuration. In an example, the energy is delivered in, on, or near a heart. At 610, a first resulting electrical signal is detected at an internal thoracic location in or near a target region of a heart. At 615, a second nondefibrillating and nonfibrillation-inducing energy is delivered to the thorax using a second electrode configuration. The second electrode is physically and/or electrically different from the first electrode configuration. In an example, the first and second energies are delivered using the same electrodes, but the electrode's position and/or orientation of the electrodes during delivery of the second energy differs from the position and/or orientation of the electrodes during delivery of the first energy. The first energy and second energy optionally have the same magnitude. At 620, a second resulting electrical signal is detected at the internal thoracic location. At 625, an electrode configuration that produces a smaller defibrillation threshold is selected for delivery of an antitachyarrhythmia therapy. In an example, selecting a configuration with a lower defibrillation threshold increases the longevity of a device, because less battery energy is used to deliver a therapy. In an example, three or more electrode configurations or combinations of electrodes are compared. In an example, a defibrillation threshold is estimated using at least one of the first and second resulting electrode signals. In an example, the first and second energy are the same magnitude (e.g. same charged capacitor voltage or same number of Joules), and the defibrillation threshold is estimated for the electrode configuration that yields a larger resulting signal.

While various operations in FIGS. 3, 4, 5, and 6 are shown as alternatives, it is understood that various operations can be performed in combination with other operations.

It is to be understood that the above description is intended to be illustrative, and not restrictive. Since many embodiments of the invention can be made without departing from the scope of the invention, the invention resides in the claims hereinafter appended.

What is claimed is:

1. A method comprising:
   delivering a first nondefibrillating and nonfibrillation-inducing energy at a first internal thoracic location at one of a right or left region of the heart;
   detecting a first resulting electrical signal at a second internal thoracic location in or near a target region of a heart to be defibrillated, wherein the target region is located at the opposite region of the heart from the region at which the energy was delivered, the first resulting electrical signal providing an indication of a first electric field strength in the target region; and
   estimating a defibrillation threshold using the first nondefibrillating and nonfibrillation-inducing energy, the first resulting electrical signal, and a target electric field strength at the target region of the heart.

2. The method of claim 1, wherein delivering a first nondefibrillating and nonfibrillation-inducing energy includes delivering the energy at a location in or near the heart.

3. The method of claim 1, wherein delivering a first nondefibrillating and nonfibrillation-inducing energy includes delivering the energy at a subcutaneous location outside the heart.

4. The method of claim 1, wherein delivering a first nondefibrillating and nonfibrillation-inducing energy includes delivering the energy at a location in or near a right region of the heart; and
   detecting a first resulting electrical signal includes detecting the signal at a location in or near a left region of the heart.

5. The method of claim 4, wherein detecting a first resulting electrical signal includes detecting the signal at a location in or near a left apical region of the heart.

6. The method of claim 4, wherein detecting a first resulting electrical signal includes detecting a signal at a location in or near a left ventricular free lateral wall of the heart.

7. The method of claim 1, wherein detecting a first resulting electrical signal at a second internal thoracic location in or near a target region of a heart includes obtaining at least two potential gradient vectors using at least three electrodes, and estimating the defibrillation threshold includes:
   combining the at least two potential gradient vectors to obtain a combined potential gradient value; and
   using the combined potential gradient value to estimate the defibrillation threshold.

8. The method of claim 1, wherein detecting a first resulting electrical signal includes detecting the first resulting electrical signal using electrodes of a bipolar lead in or near the left side of the heart.

9. The method of claim 1, further comprising delivering a notification if the estimated defibrillation threshold meets or exceeds at least one of a specified value or a specified change in value.

10. The method of claim 1, further comprising adjusting a defibrillation therapy energy to meet or exceed the first defibrillation threshold.

11. The method of claim 1, further comprising:
    delivering a second nondefibrillating and nonfibrillation-inducing energy at the first internal thoracic region; and
    detecting a second resulting electrical signal at a third internal thoracic location in or near the target region;
    wherein the estimating a defibrillation threshold includes using both the first resulting electrical signal and the second resulting electrical signal to estimate the defibrillation threshold.

12. The method of claim 1, further comprising:
    delivering a second nondefibrillating and nonfibrillation-inducing energy at the first internal thoracic region; and
    detecting a second resulting electrical signal at a third internal thoracic location in or near the target region;
    wherein the estimating a defibrillation threshold includes using a smaller of the first resulting electrical signal and the second resulting electrical signal.

13. The method of claim 1, wherein detecting a first resulting electric signal includes sensing an electrical signal through a guide wire.

14. The method of claim 1, wherein delivering a first nondefibrillating and nonfibrillation-inducing energy includes delivering the energy during a specified portion of a cardiac cycle or respiratory cycle.

15. The method of claim 1, wherein detecting a first resulting electrical signal includes detecting the first resulting electrical signal during a specified portion of a cardiac cycle or respiratory cycle.

16. The method of claim 1, wherein estimating a defibrillation threshold includes separating from the first resulting electrical signal at least one intrinsic electrical signal and using a resulting remainder of the resulting electrical signal to estimate the defibrillation threshold.

17. A method comprising:
    delivering a first nondefibrillating and nonfibrillation-inducing energy at a first internal thoracic location at one of a right or left region of the heart;
    detecting a first resulting electrical signal at a second internal thoracic location in or near a target region of a heart to be defibrillated, wherein the target region is located at the opposite region of the heart from the region at which the energy was delivered, the first resulting electrical signal providing an indication of a first electrical field strength in the target region; and
    estimating a first defibrillation threshold using the first nondefibrillating and nonfibrillation-inducing energy, the first resulting electrical signal, and a target electric field strength;
    delivering a second nondefibrillating and nonfibrillation-inducing energy at the first internal thoracic location;
    detecting a second resulting electrical signal at the second internal thoracic location, the second resulting electrical signal providing an indication of a second electric field strength in the target region of the heart during delivery of the second nondefibrillating and nonfibrillation-inducing energy;
    determining a change in a defibrillation threshold using the first resulting electrical signal and the second resulting electrical signal.

18. The method of claim 17, wherein determining a change in the defibrillation threshold includes:
    estimating a second defibrillation threshold for the target region of the heart using the indication of a second electric field strength and the second energy; and
    determining a change in a defibrillation threshold using the second defibrillation threshold and the first defibrillation threshold.

19. The method of claim 17, wherein determining a change in the defibrillation threshold includes comparing the second resulting electrical signal and the first resulting electrical signal.

20. The method of claim 17, further comprising delivering a notification if the second defibrillation threshold exceeds at least one of the first defibrillation threshold by a specified amount or a specified change from first defibrillation threshold.

21. The method of claim 17, further comprising detecting a physiological parameter using at least one other physiologic sensor; and
   delivering a notification or adjusting a defibrillation therapy if the physiological parameter meets a specified criteria the second defibrillation threshold exceeds at least one of the first defibrillation threshold by a specified amount or a specified change from first defibrillation threshold.

22. A method comprising:
   delivering a first nondefibrillating and nonfibrillation-inducing energy to a first internal thoracic location at one of a right or left region of the heart using a first defibrillation configuration;
   detecting a first resulting electrical signal at a internal thoracic location in or near a target region of a heart to be defibrillated, wherein the target region is located at the opposite region of the heart from the region at which the first energy was delivered, the first resulting electrical signal providing an indication of a first electric field strength in the target region;
   delivering a second nondefibrillating and nonfibrillation-inducing energy to a second internal thoracic location at one of a right or left region of the heart using a second defibrillation configuration;
   detecting a second resulting electrical signal at the opposite region of the heart from the region at which the second energy was delivered, the second resulting electrical signal providing an indication of a second electric field strength in the target region of the heart during delivery of the nondefibrillating and nonfibrillation-inducing energy using the second defibrillation configuration; and
   estimating at least one defibrillation threshold using at least one target electric field strength and at least one of the first and second resulting electrical signals.

23. The method of claim 22, wherein delivering a first nondefibrillating and nonfibrillation-inducing energy to a thorax using a first defibrillation configuration includes delivering the energy through a plurality of electrodes, and
   delivering a second nondefibrillating and nonfibrillation-inducing energy to the thorax using a second defibrillation configuration includes changing a configuration of the plurality of electrodes and then delivering the energy through the plurality of electrodes.

24. The method of claim 23, wherein changing a configuration of the plurality of electrodes includes changing a location of at least one electrode.

25. The method of claim 23, wherein changing a configuration of the plurality of electrodes includes electrically connecting at least one electrode to at least one other electrode.

26. The method of claim 22, wherein delivering a first nondefibrillating andnonfibrillation-inducing energy includes delivering an energy, voltage, or current using at least one electrode, and
   delivering a second nondefibrillating and nonfibrillation-inducing energy includes delivering a different energy, voltage, or current using the at least one electrode.

27. The method of claim 22, wherein delivering a first nondefibrillating and nonfibrillation-inducing energy includes delivering the first nondefibrillating and nonfibrillation-inducing energy using a first electrode configuration, and
   delivering a second nondefibrillating and nonfibrillation-inducing energy includes delivering the second nondefibrillating and nonfibrillation-inducing energy using a second electrode configuration; and
   estimating at least one defibrillation threshold selecting an electrode configuration that produces a smaller defibrillation threshold for delivery of an antitachyarrhythmia therapy therefrom.

28. A system comprising:
   an energy module adapted to deliver a nondefibrillating and nonfibrillation-inducing energy using at least a first electrode at a first internal thoracic location at one of a right or left region of the heart;
   a response signal module adapted to detect a resulting signal using at least a second electrode at a second internal thoracic location in or near a target region of a heart to be defibrillated, wherein the target region is located at a the opposite region of the heart from the region at which the energy was delivered, the responsive signal resulting from the delivery of the energy and providing an indication of an electric field strength at the second internal thoracic location; and
   a controller communicatively coupled to the energy module and the response signal module, the controller adapted to estimate a defibrillation threshold using the nondefibrillating and nonfibrillation-inducing energy and the resulting signal.

29. The system of claim 28, further comprising the first electrode, the second electrode, the response signal module adapted to detect a voltage between the second electrode and a third electrode at a location in or on the left side of the heart at a known or estimated distance from the second electrode.

30. The system of claim 29, wherein the second and third electrode are shaped and configured for implantation in or on a left apical region of the heart or a left ventricular free lateral wall.

31. The system of claim 28, further comprising a lead positionable in a coronary vessel in the left side of the heart, wherein the response signal module is adapted to detect resulting signals at multiple points in the coronary vessel, and the controller is adapted to estimate a defibrillation threshold using the responsive signals detected by the response signal module.

32. The system of claim 28, wherein the controller is adapted to compare a detected resulting signal with a previous detected resulting signal to detect a change in the resulting signal indicative of a defibrillation threshold change, physiological change, posture change, or lead dislodgement.

33. The system of claim 28, wherein the controller is adapted to compare an estimated defibrillation threshold to a previously estimated defibrillation threshold to detect a change in the defibrillation threshold.

34. The system of claim 33, wherein the controller is adapted to deliver a notification if an changed defibrillation threshold is detected.

35. The system of claim 33, wherein the controller is adapted to increase an energy level of an antitachyarrhythmia therapy if an increased defibrillation threshold is detected.

36. The system of claim 28, wherein the controller is configured to change an electrode configuration, estimate a second defibrillation threshold for at least a second electrode configuration, compare estimated defibrillation thresholds for at least two electrode configurations, and select a defibrillation electrode configuration using the estimated defibrillation thresholds.

37. The system of claim 28, further including an intrinsic heart signal sensing circuit, the controller communicatively coupled to the intrinsic heart signal sensing circuit and adapted to deliver the energy at a specified portion of a cardiac cycle or respiratory cycle.

38. The system of claim 28, further including an intrinsic heart signal sensing circuit, the controller communicatively coupled to the intrinsic heart signal sensing circuit and adapted to detect the resulting electric signal at a specified portion of a cardiac cycle or respiratory cycle.

39. The system of claim 28, further comprising the first electrode and the second electrode.

40. The system of claim 28, wherein the first internal thoracic region is in or near the right side of the heart and the second internal thoracic region is in or near the left side of the heart.

* * * * *

UNITED STATES PATENT AND TRADEMARK OFFICE
CERTIFICATE OF CORRECTION

PATENT NO. : 7,711,425 B2  Page 1 of 1
APPLICATION NO. : 11/208923
DATED : May 4, 2010
INVENTOR(S) : Xuan Wei et al.

It is certified that error appears in the above-identified patent and that said Letters Patent is hereby corrected as shown below:

In column 9, line 29, delete "nonfibriulation" and insert -- nonfibrillation --, therefor.

In column 9, lines 64-67 and in column 10, lines 1-24, below "moved." delete "Referring now to FIGS. 2A and 2C, in an example, a defibrillation threshold is determined using two or more resulting electrical signals corresponding to two or more sensor electrode configurations. FIG. 2C shows the same components as FIG. 2A but in a different configuration: lead 180 and electrodes 185 and 190 are positioned further from the apex 191 of the heart in FIG. 2C than in FIG. 2A. In an example, a nondefibrillating and nonfibrillation-inducing energy is delivered with the electrodes in the configuration shown in FIG. 2C, and then the lead 180 is inserted further into a blood vessel on the heart until the electrodes are positioned in the configuration shown in FIG. 2A, at which time another nondefibrillating and nonfibrillation-inducing energy is delivered. Resulting electrical signals are detected using both lead configurations. A defibrillation threshold energy is estimated using one or both of the corresponding resulting electrical signals. In an example, more than two configurations of lead 180 are used. In another example, resulting electrical signals are detected occasionally, periodically, or continuously as lead 180 is inserted into a vessel or into the heart. Electrical signals at different locations can be used, for example, to assess electric fields at different locations of the left ventricle free wall or the apical region and find the minimum electric field in the target region. In another example, the resulting electric field in different directions is used to estimate an electric field strength projected in the strongest direction. In an example, lead 110 is maintained in a fixed position as lead 180 is moved."

In column 17, line 62, in Claim 26, delete "andnonfibrillation" and insert -- and nonfibrillation --, therefor.

In column 18, line 22, in Claim 28, delete "a the" and insert -- the --, therefor.

Signed and Sealed this

Twenty-seventh Day of July, 2010

David J. Kappos
*Director of the United States Patent and Trademark Office*